United States Patent [19]

Barone

[11] Patent Number: 5,262,548

[45] Date of Patent: Nov. 16, 1993

[54] PHOSPHOROUS/VANADIUM OXIDATION CATALYST

[75] Inventor: Bruno J. Barone, Houston, Tex.

[73] Assignee: Scientific Design Company, Inc., Little Ferry, N.J.

[21] Appl. No.: 923,508

[22] Filed: Aug. 3, 1992

Related U.S. Application Data

[62] Division of Ser. No. 733,827, Jul. 22, 1991, Pat. No. 5,158,923, which is a division of Ser. No. 526,457, May 21, 1990, Pat. No. 5,070,060.

[51] Int. Cl.$^5$ .................................. C07D 307/60
[52] U.S. Cl. ................................... 549/262; 549/231; 549/232; 549/240; 549/247; 549/248; 549/249; 549/256; 549/257; 549/258; 549/259; 549/260; 549/261; 562/483; 562/512.4
[58] Field of Search ............... 562/483, 512.4; 549/231, 232, 240, 247–249, 256–262

[56] References Cited

U.S. PATENT DOCUMENTS

| | | | |
|---|---|---|---|
| 3,255,211 | 6/1966 | Kerr | 260/346.8 |
| 3,297,587 | 1/1967 | Scherhag et al. | 252/432 |
| 3,684,741 | 8/1972 | Friedrichser et al. | 252/435 |
| 3,956,181 | 5/1976 | Grasselli et al. | 252/432 |
| 3,980,585 | 9/1976 | Kerr et al. | 252/437 |
| 4,017,521 | 4/1977 | Schneider | 260/346.8 A |
| 4,043,943 | 8/1977 | Schneider | 252/437 |
| 4,056,487 | 11/1977 | Kerr | 252/435 |
| 4,147,661 | 4/1979 | Higgins et al. | 252/435 |
| 4,167,516 | 9/1979 | Kerr | 252/432 |
| 4,251,390 | 2/1981 | Barone | 252/435 |
| 4,283,307 | 8/1981 | Barone et al. | 252/432 |
| 4,418,003 | 11/1983 | Udovich et al. | 502/209 |
| 4,515,899 | 5/1985 | Click et al. | 502/35 |
| 4,515,904 | 5/1985 | Edwards | 502/209 |

Primary Examiner—Cecilia Tsang
Attorney, Agent, or Firm—Kenneth H. Johnson

[57] ABSTRACT

An improvement in the oxidation catalyst used for the partial oxidation of n-butane and containing vanadium and phosphorus, zinc and lithium mixed oxides which comprises adding a molybdenum compound modifier in an amount of from about 0.005 to 0.025/1 Mo/V to the catalyst during the digestion of the reduced vanadium compound by concentrated phosphoric acid. The addition of Mo produces a catalyst which is very stable more active system and longer lived than the unmodified catalyst.

22 Claims, No Drawings

PHOSPHOROUS/VANADIUM OXIDATION CATALYST

This is a division of application Ser. No. 07/733,827, filed Jul. 22, 1991 now U.S. Pat. No. 5,158,923, which is a division of application Ser. No. 07/526,457, filed May 21, 1990, now U.S. Pat. No. 5,070,060.

BACKGROUND OF THE INVENTION

The present invention relates to an improved PVO-zinc activated, lithium modified catalyst for use the in the partial oxidation of hydrocarbons to prepare dicarboxylic acids and anhydrides. More particularly, the invention relates to the improved phosphorus-vanadium mixed oxide catalyst prepared in an anhydrous system.

Basically, all of the methods used to prepare oxidation catalysts seek to obtain vanadium in a valence state of less than +5. One method of achieving this is to begin with vanadium in less than the +5 valence state. Another method and that used most widely in the art is to start with vanadium in the +5 state and reduce the valency to less than +5. This invention relates to the latter method. Several variations on this method have been used to obtain these catalyst. In one method $V_2O_5$ is reduced in a solution with HCl to obtain vanadyl chloride. A typical catalyst preparation may involve dissolving the vanadium, phosphorus, and other components in a common solvent. The reduced vanadium with a valence of less than 5 is obtained by initially using a vanadium compound with a valence of plus 5 such as $V_2O_5$ and thereafter reducing to the lower valence with, for example, hydrochloric acid during the catalyst preparation to form the vanadium oxysalt, vanadyl chloride, in situ. The vanadium compound is dissolved in a reducing solvent, such as hydrochloric acid, which solvent functions not only to form a solvent for the reaction, but also to reduce the valence of the vanadium compound to a valence of less than 5. Preferably, the vanadium compound is first dissolved in the solvent and thereafter the phosphorus and other components, if any, are added. The reaction to form the complex may be accelerated by the application of heat. The complex formed is then, without a precipitation step, deposited as a solution onto a carrier and dried. Generally, the average valence of the vanadium will be between about plus 2.5 and 4.6 at the time of deposition onto the carrier.

In another method the catalyst is prepared by precipitating the metal compounds, either with or without a carrier, from a colloidal dispersion of the ingredients in an inert liquid. In some instances the catalyst may be deposited as molten metal compounds onto a carrier. The catalysts have also been prepared by heating and mixing anhydrous forms of phosphorus acids with vanadium compounds and other components. In any of the methods of preparation, heat may be applied to accelerate the formation of the complex.

A method of obtaining vanadyl chloride was disclosed by Koppel et al, Zeit. anorg. Chem, 45, p. 346-351, 1905 by the reduction of $V_2O_5$ in alcoholic HCl solution. This method has been recommended for the preparation of the phosphorus-vanadium oxidation catalyst for example, by Kerr in U.S. Pat. No. 3,255,211 where the solvent also serves as the reducing agent. Subsequently, U.S. Pat. Nos. 4,043,943, 4,251,390, 4,283,307; and 4,418,003 for example, employed this method generally referred to as the "anhydrous process" of reducing vanadium to prepare the basic phosphorus-vanadium catalyst. The catalysts produced by this latter method have been found to be generally superior to similar catalyst by the other methods. Specifically what had occurred to this class of oxidation catalysts prior to the return to the anhydrous process had been the addition of a veritable cornucopia of elements to the base vanadium-phosphorus composition, see for example U.S. Pat. No. 4,105,586 where in addition to V, P and O the catalyst must contain nine other elements. The catalyst were satisfactory, but manufacturing was difficult because of the number of components and their varying effects on the catalyst performance.

The anhydrous system went back to the basics with the Schneider procedure in U.S. Pat. No. 4,043,943 with only V, P and O. However, this catalyst required a very specific activation procedure as described, for example in U.S. Pat. No. 4,017,521. Barone (U.S. Pat. No. 4,251,390) showed that the addition of Zn alleviated the need for the specific activation process and produced a catalyst which was more easily activated and which was very stable to heat upset of the reaction system as well as exhibiting equal or superior performance (conversion/selectivity/yield) to the base catalyst. Small amounts of silicon and lithium compounds were also found to enhance the catalytic effects of P/V/Zn catalyst.

U.S. Pat. No. 4,147,661 discloses high surface area PVO mixed oxide catalyst additionally containing W, Sb, Ni and/or Mo at atonic ratios of 0.0025 to 1:1 to vanadium.

A particular problem facing all of the PVO containing catalysts is the loss of phosphorus, a discussion of this problem and various solutions is found in U.S. Pat. No. 4,515,899.

Many references disclosing oxidation catalysts which are suitable for producing maleic anhydride by the partial oxidation of n-butane, which catalysts contain molybdenum as one component of a phosphorus, vanadium mixed oxide catalyst. For example U.S. Pat. No. 3,980,585 discloses a catalyst containing P, V Cu and one of Te, Zr, Ni, Ce, W, Pd, Ag, Mn, Cr, Zn, Mo, Re, Sn, La, Hf Ta, Th, Ca, U or Sn; and U.S. Pat. No. 4,056,487 discloses a PVO catalyst containing Nb, Cu, Mo, Ni, Co and plus one or more of Ce, Nd, Ba, Hf, U, Ru, Re, Li or Mg. U.S. Pat. No. 4,515,904 discloses a procedure for preparing PVO catalysts which may include one metal of Mo, Zn, W, U, Sn, Bi, Ti, Zr, Ni, Cr or Co in atomic ratios of metal: V of 0.001 to 0.2:1.

U.S. Pat. No. 4,418,003 discloses PVO catalysts containing either Zn or Mo which is deactivated by Na or Li and which may also contain Zr, Ni, Ce, Cr, Mn, Ni and Al.

U.S. Pat. No. 4,251,390 discloses anhydrous process PVO oxidation catalyst activated with Zn and modified with Li or Si.

It is a feature of the present invention that the addition of a specific modifier to the phosphorus/vanadium/zinc/lithium mixed oxide catalyst produces catalysts of greater stability which give high yields of anhydride for long periods of time.

It is a further feature of the present catalyst that lower P/V ratios than unmodified catalysts are suitable with the concomitant reduction in the loss of phosphorus from the catalyst in operation.

SUMMARY OF THE INVENTION

The present invention lies in an improvement in anhydrous process phosphorus/vanadium/zinc/lithium mixed oxide oxidation catalyst containing from 0.005 to 0.025 atoms of molybdenum per atom of vanadium. The present catalysts are produced by the process comprising reducing vanadium in the +5 valence state in a substantially anhydrous organic medium to a valence of less than +5 and digesting said reduced vanadium in concentrated phosphoric acid wherein the improvement comprises including a molybdenum compound in the mole ratio to vanadium in the ranges of 0.005 to 0.025:1, preferably 0.01 to 0.020:1 thereby obtaining a easily activated catalyst having superior resistance to deactivation by impurities and excessive heat during use and higher and longer productivity. Suitable dried catalysts have a crystallinity of 60 to 90%, preferably at least 70%.

PREFERRED EMBODIMENTS

More specifically, the improved catalyst is that produced from an alcoholic HCl solution reduction of vanadium pentoxide wherein the organic solvent is an alcohol and the reduction of the vanadium is obtained by contacting it with HCl. This is conveniently carried out by passing gaseous HCl through the alcohol having the vanadium pentoxide suspended therein. The vanadium pentoxide is reduced by the HCl and brought into solution as the vanadyl chloride. The completion of the reduction is the appearance of a dark reddish brown solution. Hydrogen bromide would be about the same as a reducing agent in this system. It is preferred that the reduction temperature should be maintained at no greater than 60° C. and preferably less than 55° C. Optimally active catalyst are the result when the reduction is carried out temperatures in the range of about 35° C. to 55° C., preferably 40° C. to 55° C.

Generally in the catalyst preparation from 2500 to 4400 ml of alcohol, preferably 3100 to 4200 ml per pound of $V_2O_5$ and from 1.5 to 3.0 pounds of HCl per pound of $V_2O_5$ are employed.

To obtain the mixed oxides of vanadium and phosphorus, phosphoric acid of approximately 99% $H_3PO_4$ (98 to 101%) is added, for example, prepared from 85 $H_3PO_4$ and $P_2O_5$ or commercial grades of 105 and 115% phosphoric acid diluted with 85% $H_3PO_4$ and the Vanadium compound digested which is discerned by a change in the color of the solution to a dark blue green. The alcohol is then stripped off to obtain the dried catalyst.

The digestion of the vanadium compound in the phosphoric acid is normally conducted at reflux until the color change indicated the completed digestion. However, about one hour under these conditions appears to produce the best catalyst. Alternately, equally good catalyst were obtained without reflux digestion by a slow boil up for about 1 to 2 hours with continuous removal of the alcohol, at which time the temperature was increased and the stripping intensified as in a normal alcohol recovery operation.

The alcohol stripping should be conducted to avoid the formation of a crust in the stripper and to produce a flowable slurry. Catalysts prepared from a procedure where a crust has formed has been found to be less active.

The final removal of alcohol is carried out under reduced pressure in an oven generally at temperatures in the range of 110° to 170° C., hence lower temperatures and less rigorous conditions are employed than in the stripping.

It was found that the roasting of the recovered dried catalyst in a flue gas oven for 3 hours at 260° C. produced a more active catalyst than a conventional calcination at 325° C. in a muffle furnace for 1¼ hours. Any activation which will provide comparable conditions can be used, however, the experienced practitioner will evaluate the various combinations to optimize the resultant catalyst performance. Generally calcination or roasting will be at a temperature in the range of 200° to 350° C. for a sufficient period to improve the catalytic properties of the composition.

The temperatures employed are relatively low hence the term calcination may not be appropriate. In any event, heating the composition under these temperature conditions has been found beneficial. The calcination is preferably carried out to produce materials having a characteristic powder x-ray diffraction ratio of 1.75 to 2.5.

The organic solvent is preferably a primary or secondary alcohol such as methanol, ethanol, 1-propanol, 2-propanol, butanol, 2-butanol, 2,methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, 1,2-ethanediol, glycerol, trimethylopropane, diethylene glycol and triethylene glycol. The alcohol is also a mild reducing agent for the vanadium +5 compound.

Generally the atomic ratio of Zn to vanadium is in the range of 0.001 to 0.15:1, however it has been found that lower ratios of zinc/vanadium produce the most active catalyst and compositions containing Zn/V mole ratio in the range of 0.01 to 0.07 are preferred.

The phosphorus is generally present in these catalyst as well as those of the prior art in the mole ration of P/V 0.09–1.3/1. Optimum ratios P/V are found to be below 1.22/1 and above 1.0/1. The stabilizing effect of Mo allows the use of less phosphorus than otherwise comparable prior art catalyst and the concomitant benefit that phosphorus loss and the resulting deactivation of the catalyst in reactor operation is reduced, i.e., longer time trend (reactivity vs hours on stream).

The lithium component is present at an atomic ratio of 0.001 to 0.15:1, Li:V.

The point at which the zinc component, lithium component and molybdenum component is added is not critical so long it is present prior to formation of the solid catalyst precipitate. This is conveniently done along with the phosphoric acid addition, thereby assuring the intimate mixing of the catalyst components.

The modifier components are added as the compounds thereof such as acetates, carbonates, chlorides, bromides, oxides, hydroxides, phosphates and the like e.g., zinc chloride, zinc oxide, zinc oxalate, lithium acetate, lithium chloride, lithium bromide, lithium carbonate, lithium oxide, lithium orthophosphate, molybdenum oxide, molybdenum dioxydichloride, molybdenum dioxydibromide and the like.

The resultant catalyst complex is characterized as a mixed oxide, however, the structure of the complex has not been determined but may be conveniently represented by a formula such as:

$$V\ P_a\ Zn_b\ Mo_c\ Li_d\ O_x$$

a is 0.90 to 1.3, b is 0.001 to 0.15, c is 0.005 to 0.025 and d is 0.001 to 0.15. This representation is not an empirical formula and has no significance other than representing the atom ratio of the components of the catalyst. The x in fact, has no determinate value and can vary widely depending on the combinations within the complex. That there is oxygen present is known, and the $O_x$ is representative of this.

The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307 which is incorporated herein. The material can be deposited on a carrier, however, when the feed to the reaction is an alkane such as n-butane for the production of maleic anhydride, this is not a desirable arrangement. If the feed was an alkene such as an n-butene the supported catalyst would be a reasonable and economic approach. Since the alkane requires a higher level of activation than the alkenes, it is desirable in the case of a feed of the former to have the catalyst present in an unsupported form in order to provide more sites for activation of the reaction with oxygen. Generally, the unsupported catalyst will have higher surface area than supported catalysts. The final catalyst particle size for this arrangement is usually about 2½ to about 10 mesh however, a high surface area is not desirable, possibly because of the enhanced activity of the catalyst from the molybdenum. In any event after activation the surface area is preferably less than 20 m²/g and at least 1 m2/g, preferably at least 5 m2/g.

Although fixed bed tubular reactors are standard for this type of reaction, fluidized beds are frequently used for oxidation reactions, in which case the catalyst particle size would be on the order of about 10 to 150 microns.

The use of this class of catalyst for the partial oxidation of $C_4$-$C_{10}$ hydrocarbons to the corresponding anhydrides is generally recognized. They have been widely considered for the conversion of normal $C_4$ hydrocarbons, both the alkane, n-butane, and alkene, n-butene, for the production of maleic anhydride, which has a wide commercial usage.

The oxidation of the n-$C_4$ hydrocarbon to maleic anhydride may be accomplished by contacting, e.g., n-butane in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the standard tubular oxidation reactors normally will contain air and about 0.5 to about 2.5 mole percent hydrocarbons such as n-butane. About 1.0 to about 2.0 mole percent of the n-$C_4$ hydrocarbon are satisfactory for optimum yield of product for the process of this invention. Although higher concentrations may be employed, explosive hazards may be encountered except in fluidized bed reactors where concentrations of up to about 4 or 5 mole % can be used without explosive hazard. Lower concentrations of $C_4$, less than about one percent, of course, will reduce the total productivity obtained at equivalent flow rates and thus are not normally economically employed.

The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the catalyst of the present invention for conversion to maleic anhydride is a n-$C_4$ hydrocarbon comprising a predominant amount of n-butane and more preferably at least 90 mole percent n-butane.

A variety of reactors will be found to be useful and multiple tube heat exchanger type reactors are quite satisfactory. The tubes of such reactors may vary in diameter from about ¼ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrite eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbonsteel and nickel tubes have excellent long life under the conditions for the reactions described herein. Normally, the reactors contain a preheat zone of an inert material such as ¼ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions, in a preferred procedure, the temperature in the center of the reactor, measured by thermocouple, is about 365° C. to about 550° C. The range of temperature preferably employed in the reactor, measured as above, should be from about 380° C. to about 515° C. and the best results are ordinarily obtained at temperatures from about 390° C. to about 415° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 470° C. for extended lengths of time because of decreased yields and possible deactivation of the catalyst.

Generally the improved catalyst of the present invention is more active and operates at a lower temperature and higher weight yield than prior anhydrous process PVO catalysts.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered in a number of ways well known to those skilled in the art. For example, the recovery may be by direct condensation or by adsorption in suitable media, with subsequent separation and purification of the maleic anhydride.

Reactors

The Reactors are 5 to 12 foot tubes having 1 inch outside diameter as specified below. For example, a 5 foot carbon steel tube, 1 inch outside diameter, reactor employed 320 milliliters of catalyst in a 3.5 foot bed packed with inert ¼ inch Alundum pellets on top of the catalyst material to a height 33% of the height of the catalyst. For each reactor, the catalyst material and inerts above are:

| length | diameter | Cat. Size | ml catalyst | inert top packing |
|---|---|---|---|---|
| 5' × 1" OD | | 3/16" × 3/16" | 320 | ¼" Alundum¹ pellets, ⅛ catalyst bed |
| 12' × 1" | | 3/16" × 3/16" | 950 | ¼" Alundum pellets, 12" at Bottom 6" at Top |

The reactors were encased in a 7% sodium nitrate —40% sodium nitrite —53% potassium nitrite eutectic mixture constant temperature salt bath. The reactor was slowly warmed to 400° C. (250°–270° C. air passing over catalyst) while passing a gas stream containing 0.5 to 0.7 mole percent n-butane and air over the catalyst beginning at about 280° C. The reactor outlet was maintained at 1 psig. After the reactor had reached 400° C., the catalyst was aged by passing the n-butane/air mixture therethrough for 24 hours. The n-butane/air and temperature were increased to obtain a desired throughput. The n-butane in the feed is increased to 1.0–1.5 mole percent to obtain 80–90% conversion. The salt bath is operated at a maximum of 425° C. The throughput is achieved in relation to the maximum salt bath temperature and maximum hot spot of about 450° C. The hot spot is determined by a probe through the center of the catalyst bed. The temperature of the salt bath can be adjusted to achieve the desired relationship between the conversion and flow rates of the n-C₄/air mixture (e.g. gas hourly space velocity - GHSV). The flow rate is adjusted to about 85% conversion and the temperature relations given above. Generally, flow rates of about 30 to 75 grams of hydrocarbon feed per liter hour are used. The exit gases were cooled to about 55°–60° C. at about ½ psig. Under these conditions, about 30–50% of the maleic anhydride condenses out of the gas stream. A water scrubber recovery and subsequent dehydration and fractionation were used to recover and purify the remaining maleic-anhydride in the gas stream after condensation. The combined maleic anhydride recovered is purified and recovered at a temperature of about 140°–150° C. overhead and 145° C. bottoms temperatures in a fractionator. The purified product had a purity of 99.9+ percent maleic anhydride.

Catalyst Scale up Procedure

Scale up studies indicate that a high agitation ratio and more rapid stripping of the alcohol produce a better catalyst. For example, in a 2000 gallon commercial pfaudler reactor at least a stirring rate of 118 RPM would be needed and the steam pressure regulated to achieve the desired rapid stripping of the alcohol while avoiding overloading the apparatus condenser. Otherwise the scale procedure is substantially the same as that described, with the further proviso that a higher concentration of alcohol may be required to insure good mixing and stripping the alcohol and removing water.

The method in which the catalyst is prepared is important. Various improvements and perimeters are disclosed above, which when employed in the general procedure will produce superior, stable, long lived catalyst. The following typical catalysts preparative procedures illustrate typical catalyst work up using the information discussed above.

CATALYST PREPARATION FOR EXAMPLE 1

Into a 5 liter glass reactor was charged 1.800 liters of anhydrous isobutyl alcohol and 1.75 moles of vanadium pentoxide. The reactor was equipped with overhead stirrer, gas inlet, thermowell and a Dean Stark trap with water condenser. 4.77 grams of anhydrous zinc chloride, 1.48 grams of lithium chloride and 6.29 grams of molybdenum oxide were added and approximately 2.0 lbs. of HCl gas were passed through the stirred suspension at such a rate as to maintain a reaction temperature of about 50° C. To the resulting dark reddish brown solution was added an alcoholic solution of 99.3% phosphoric acid previously prepared by adding 104.0 g. of $P_2O_5$ to 296.1 g. of 85.7% $H_3PO_4$ until solution was complete and then diluting the acid with 400 ml of anhydrous alcohol. The resulting solution was refluxed for 2 hours. Effluent gases were scrubbed with a caustic solution. At the end of the digestion period, the alcohol was stripped until about 1.8 liters were recovered from the dark blue solution. The resulting slurry was dried at 150° C. and calcined at 260° C. for three hours. The calcined powder was formed into 3/16"×3/16" tablets with 1/16" I.D. holes struck therethrough. Atomic Ratios were:

P:V=1.16:1; Mo: V=0.013:1; Zn: V=0.01:1; Li :V=0.01:1

The tableted and cored (3/16"×3/16") catalyst had a surface area of 4.6 m²/g. X-Ray diffraction analysis of the calcined catalyst disclosed a crystalline pattern with a reflection ratio (2.94d/5.68d) of 2.6. The degree of crystallinity of the fresh catalyst was 80%.

Isobutyl alcohol was used as the organic solvent in the preparation of each of the catalyst described here.

In the following examples of n-butane partial oxidation to maleic anhydride air in the feed to the reaction is reported as "% air". 100% air=2500⁻¹ GHSV.

The catalyst is conditioned for use by placing the catalyst (tablets) in the tubular reactor of a fixed bed reactor and carrying out the conditioning. The reactor is heated by the salt bath.

The catalyst is loaded in the reactor and conditioned by a slow bring-up of the catalyst to operating temperature at the rate of 5° to 10° C. per hour achieved by heating the reactor and adjusting the gas flow from 0.5 to 1.0 mole % butane in air at an initial air flow of GHSV of 900$^{-1}$ hours up to 2500 $^{-1}$ hours while maintaining a desired conversion level, e.g., about 75 mole %, the procedure requiring in general several days. The initial temperature of the salt bath is about 250° C. (a point where the salt bath is molten).

The C, S and Y used in reporting reaction results have the following meaning and relationship C(conversion) × S(selectivity) = Y(yield).

The term "weight yield" means the amount of maleic anhydride produced from a given amount of n-butene, calculated as follows:

$$\text{wt yield} = \frac{98 \text{ (mole wt of maleic anhydride)}}{58 \text{ (mole wt of butane)}} \times \text{mole \% yield}$$

Peak-heights above background are measured from duplicate diffraction patterns to calculate the Reflection Ratio 2.94d/5.68d.

Percent crystallinity is determined by comparing the intensity of the 2.94d reflection of the dried catalyst material to that of a secondary standard of VOHPO$_4$.½ H$_2$O.

EXAMPLE 1

The catalyst prepared as described above was loaded into a 5' salt bath unit. It activated very well, reaching full flow after 418 hours on stream. This catalyst was on stream for 4600 hours. At shut down the average weight yield was 93.5% at 82.8% conversion at 372° C. At 3000 hours it was operating at a low salt temperature of 378° C. with an average weight yield of 96.0 at 81.9 conversion. There was no apparent yield decay. At 4300 hours the average yield was 93.6% at 83.2% conversion. This run is summarized in TABLE I.

TABLE I$^{(1,2)}$

| ON STREAM HRS. | TEMP C. SALT | TEMP C. HOT SPOT | BUTANE FEED M % | GHSV 1/HR | BUTANE CONV. M % | MAN PROD. SELE M % | MAN PROD. YLD. M % | MAN PROD. YLD. WT % | PRESS. PSIG. HD |
|---|---|---|---|---|---|---|---|---|---|
| 46 | 400 | 404 | 0.63% | 1500 | 68.1 | 60.9 | 41.5 | 70.2 | 5 |
| 418 | 415 | 455 | 1.11 | 2500 | 80.4 | 64.0 | 51.5 | 87.0 | 20 |
| 1400–1500 | 383 | 432 | 1.27 | 2500 | 79.9 | 71.4 | 57.1 | 96.4 | 20 |
| 2900–3000 | 378 | 438 | 1.33 | 2500 | 81.9 | 69.4 | 56.8 | 96.0 | 20 |
| 4200–4300 | 374 | 443 | 1.28 | 2500 | 83.18 | 66.61 | 55.40 | 93.6 | 20 |
| 4500–4600 | 372 | 440 | 1.31 | 2500 | 82.8 | 66.8 | 55.3 | 93.5 | 20 |
| TERMINATED | | | | | | | | | |
| CONTROL$^{(3)}$ | | | | | | | | | |
| 1500 | 390 | — | — | — | 78.7 | 65.5 | — | 87.0 | — |

$^{(1)}$VP 1.16, Mo 0.013, Zn 0.01, Li 0.01, o$_x$.
$^{(2)}$1" × 5' Reactor-3.5' bed with thermowell-3/16" × 3/16" tablets with 1/16" hole in center.
$^{(3)}$VP 1.16, Zn 0.01, Li 0.01, O$_x$ - U.S. Pat. No. 4,251,390.

EXAMPLE 2

This catalyst was prepared in the same manner as that of Example 1 in three batches which were blended. The average x-ray reflection ratio (2.94d/5.68d) of the calcined catalyst was 3.6 with little or no evidence of vanadyl dihydrogen phosphate. the surface area of the tableted catalyst was 10.6 m$^2$/g. The degree of crystallinity was 83%. This catalyst was loaded into the 1"×12' reactor and evaluated as before. This catalyst was on stream for 8386 hours. After about 2600 hours on stream the weight yield showed a slight decay trend, and at 3350 to 3525 a small amount of trimethyl phosphite (TMP) was introduced at a rate of about 0.05 ml/day. The response was immediate and weight yield rapidly increased to its previous high level. At 4500 hours on stream a small continuous flow (about 0.1 ppm) of trimethyl phosphite was added until the end of the run. This caused a slight increase in temperature (about 5° C. over normal) but maintained the high yield. The results and conditions of this evaluation are summarized in Table II.

During this run a space velocity study was carried out at both 17 and 20 psig inlet pressures. The data showed essentially the same weight yields were obtained under both pressures and only slight differences in temperature requirement noted. This study is reported in TABLE III.

TABLE II$^{(1,2)}$

| ON STREAM HRS. | TEMP C. SALT | TEMP C. HOT SPOT | BUTANE FEED M % | GHSV 1/HR | BUTANE CONV. M % | MAN PROD. SELE M % | MAN PROD. YLD. M % | MAN PROD. YLD. WT % | PRESS. PSIG. HD | PRESS. PSIG. EXIT |
|---|---|---|---|---|---|---|---|---|---|---|
| 45 | 390 | 400 | 0.72 | 1500 | 82.2 | 60.8 | 50.0 | 84.5 | 7.0 | 4.0 |
| 381 | 415 | 432 | 1.37 | 2500 | 79.4 | 63.3 | 50.2 | 84.9 | 20.0 | 15.5 |
| 2200–2300 | 383 | 434 | 1.66 | 2500 | 81.68 | 68.85 | 56.24 | 95.0 | 20.0 | 15.5 |
| 3200–3300 | 379 | 434 | 1.64 | 2500 | 82.1 | 66.8 | 54.8 | 92.6 | 20.0 | 15.5 |
| 3700–3800 | 392 | 424 | 1.65 | 2500 | 80.8 | 69.9 | 56.5 | 95.5 | 20.0 | 15.5 |
| 4400–4500 | 382 | 429 | 1.66 | 2500 | 82.88 | 67.69 | 56.10 | 94.8 | 20.0 | 15.5 |
| Note 3 | | | | | | | | | | |
| 5100–5200 | 387 | 427 | 1.61 | 2500 | 81.32 | 67.84 | 55.17 | 93.2 | 20.0 | 15.5 |
| 6800–6900 | 381 | 405 | 1.63 | 1750 | 88.59 | 68.08 | 60.31 | 101.9 | 20.0 | 16.0 |
| 8386 | 392 | 425 | 1.64 | 2500 | 86.10 | 85.25 | 56.18 | 95.0 | 20.0 | 14.0 |

TABLE II[(1,2)]-continued

| ON STREAM HRS. | TEMP C. | | BUTANE FEED M % | GHSV 1/HR | BUTANE CONV. M % | MAN PROD. | | | PRESS. PSIG. | |
|---|---|---|---|---|---|---|---|---|---|---|
| | SALT | HOT SPOT | | | | SELE M % | YLD. M % | YLD. WT % | HD | EXIT |
| | | | | Terminated | | | | | | |

[(1)]VP 1.16, Mo 0.013, Zn 0.01, Li 0.01, $O_x$
[(2)]1" × 12' reactor-10.5' bed with thermowell-3/16" × 3/16" tablets with 1/16" hole in center.
[(3)]TMP Addition initiated at 0.1 ppm rate.

TABLE III

SPACE VELOCITY STUDY[(1)]

| SPACE VELO-CITY 1/hr. | INLET PRESS PSIG | BU-TANE CONC. M % | SALT TEMP. C. | BU-TANE CONV M % | MAN YIELD WT % |
|---|---|---|---|---|---|
| 1750 | 20 | 1.69 | 383 | 89.5 | 102.5 |
| | 17 | 1.65 | 387 | 90.3 | 102.4 |
| 2000 | 20 | 1.70 | 388 | 88.7 | 102.0 |
| | 17 | 1.62 | 391 | 88.1 | 101.0 |
| 2250 | 20 | 1.65 | 397 | 89.2 | 98.9 |
| | 17 | 1.66 | 396 | 88.4 | 98.4 |
| 2500 | 20 | 1.60 | 392 | 87.1 | 95.5 |
| | 17 | 1.57 | 390 | 86.1 | 95.0 |

[(1)]Data taken from the evaluation of Example 2 between 6000–8400 hours on stream with continuous addition of TMP (0.1 ppm).

EXAMPLE 3

The procedure for making the catalyst of Example 1 was followed except that the Mo component was added after the reaction of vanadium and HCl. The calcined catalyst had a 62% crystallinity by x-ray diffraction.

was evaluated in a 5' reactor. The conditions and summarized results of the run are set out in TABLE IV.

TABLE IV[(1,2)]

| ON STREAM HRS. | TEMP C. | | BUTANE FEED M % | GHSV 1/HR | BUTANE CONV. M % | MAN PROD. | | | PRESS. PSIG. HD |
|---|---|---|---|---|---|---|---|---|---|
| | SALT | HOT SPOT | | | | SELE M % | YLD. M % | YLD. WT % | |
| 42 | 410 | 412 | 0.57 | 1500 | 45.12 | 52.52 | 23.70 | 40.1 | 4.5 |
| 48 | 420 | 437 | 0.83 | 2000 | 89.26 | 57.93 | 51.93 | 87.4 | 20 |
| 162 | 408 | 431 | 0.77 | 2000 | 81.67 | 63.97 | 52.24 | 88.3 | 20 |
| 355 | 400 | 427 | 1.16 | 2000 | 80.90 | 69.49 | 56.21 | 95.0 | 20 |
| 379 | 406 | 429 | 1.08 | 2250 | 81.15 | 65.19 | 52.90 | 89.4 | 20 |
| 481 | 407 | 433 | 1.23 | 2500 | 88.82 | 64.33 | 57.14 | 96.6 | 20 |
| 547 | 400 | 420 | 1.20 | 2500 | 82.18 | 68.18 | 56.03 | 94.7 | 20 |
| | | | | TERMINATED | | | | | |

[(1)]VP 1.16, Mo 0.013, Zn 0.01, Li 0.01, $O_x$ - $MoO_3$ added after reaction of HCl with $V_2O_5$ was completed.
[(2)]Evaluated in a 1" × 5' reactor containing a 3.5' bed with thermowell using 3/16 × 3/16" tablets with a 1/16" hole in center.

EXAMPLE 4

The procedure for making the catalyst of Example 1 was followed except that 5% additional alcohol was used in the HCl reaction. The x-ray diffraction ratio (2.94d/5.68d) of the calcined catalyst was 1.8 and crystallinity was 84%. The fresh tableted catalyst had a surface area of 3.9 m²/g. It was evaluated in a 1"×12" reactor. The conditions and summarized results are shown in TABLE V.

EXAMPLE 5

The procedure for making the catalyst of Example 1 was followed except that 5% less alcohol was used in the HCl reaction. The x-ray diffraction ratio (2.94d/5.68d) of the calcined catalyst was 1.63 and crystallinity was 87%. The fresh tableted catalyst had a surface area of 6.9 m²/g. It was evaluated in a 1"×12' reactor. The conditions and summarized results are shown in TABLE VI.

TABLE V[(1,2)]

| ON STREAM HRS. | TEMP C. | | BUTANE FEED M % | GHSV 1/HR | BUTANE CONV. M % | MAN PROD. | | | PRESS. PSIG. | |
|---|---|---|---|---|---|---|---|---|---|---|
| | SALT | HOT SPOT | | | | SELE M % | YLD. M % | YLD. WT % | HD | |
| 70 | 420 | 427 | 1.42 | 1750 | 51.06 | 54.11 | 27.63 | 46.7 | 16.0 | 13.0 |
| 200–300 | 416 | 436 | 1.49 | 2500 | 80.75 | 61.66 | 49.79 | 84.1 | 20.0 | 15.5 |
| 600–700 | 413 | 433 | 1.59 | 2500 | 77.94 | 66.01 | 51.45 | 86.9 | 20.0 | 15.5 |
| 900–1000 | 417 | 434 | 1.55 | 2500 | 81.52 | 64.72 | 52.76 | 89.2 | 20.0 | 15.5 |
| | | | | TERMINATED | | | | | | |

[(1)]$MoO_3$ added after reaction of $V_2O_5$ with HCl.5% excess alcohol added to initial reaction.
[(2)]Evaluated in a 1" × 12" reactor-10.5' bed with thermowell-3/16" × 3/16" tablets used with 1/16" hole in the center.

The reflection ratio (2.94d/5.68d) was 2.3. The sample

TABLE VI[(1,2)]

| ON STREAM HRS. | TEMP C. | | BUTANE FEED M % | GHSV 1/HR | BUTANE CONV. M % | MAN PROD. | | | PRESS. PSIG. | |
|---|---|---|---|---|---|---|---|---|---|---|
| | SALT | HOT SPOT | | | | SELE M % | YLD. M % | YLD. WT % | HD | EXIT |
| 46 | 410 | 411 | 0.67 | 1500 | 43.36 | — | — | — | 7.0 | 4.0 |
| 359 | 415 | 435 | 1.46 | 2250 | 80.71 | 63.99 | 51.65 | 87.3 | 20.0 | 16.3 |
| 400–500 | 417 | 443 | 1.47 | 2500 | 77.65 | 64.77 | 50.30 | 85.0 | 20.0 | 15.5 |
| 900–1000 | 419 | 440 | 1.57 | 2500 | 78.18 | 65.51 | 51.21 | 86.5 | 20.0 | 15.5 |

TABLE VI[(1,2)]-continued

|  | TEMP C. |  | BUTANE |  | BUTANE | MAN PROD. |  |  | PRESS. |  |
|---|---|---|---|---|---|---|---|---|---|---|
| ON STREAM |  | HOT | FEED | GHSV | CONV. | SELE | YLD. | YLD. | PSIG. |  |
| HRS. | SALT | SPOT | M % | 1/HR | M % | M % | M % | WT % | HD | EXIT |
|  |  |  |  | TERMINATED |  |  |  |  |  |  |

[(1)]MoO₃ added after reaction of V₂O₅ with HCl.5% less alcohol was added to initial reaction.
[(2)]Evaluated in a 1" × 12" reactor-10.5' bed with thermowell-3/16" × 3/16" tablets used with 1/16" hole in the center.

EXAMPLE 6

The catalyst procedure was that employed for the catalyst of Example 1, except that the Mo component was added after the alcohol solvent was heated to reflux. The digestion step was eliminated and alcohol recovery was immediately initiated. The resulting calcined catalyst had an x-ray diffraction reflection ratio (2.94d/5.68d) of 1.86 and a crystallinity of 93%. The catalyst was evaluated in a 1"×5' reactor. The conditions and summarized results are set out in TABLE VII.

EXAMPLE 7

The procedure used for the catalyst preparation of Example 1 was followed, except that twice the concentration of molybdenum was employed. The x-ray diffraction of the calcined catalyst showed a reflection ratio (2.94d/5.68d) of 1.46 with no evidence of vanadyl dihydrogen phosphate. The crystallinity was 75%. The catalyst was evaluated in a 1"×5' reactor. The conditions and summarized results are set out in TABLE VIII.

EXAMPLE 8

The procedure used for the catalyst preparation of Example 1 was followed, except that one-half the concentration of molybdenum was employed. The x-ray diffraction of the calcined catalyst showed a reflection ratio (2.94d/5.68d) of 1.8 with no evidence of vanadyl dihydrogen phosphate. The crystallinity was 92%. The catalyst was evaluated in a 1"×5' reactor. The conditions and summarized results are set out in TABLE IX.

TABLE VIII[(1,2)]

|  | TEMP C. |  | BUTANE |  | BUTANE | MAN PROD. |  |  | PRESS. |
|---|---|---|---|---|---|---|---|---|---|
| ON STREAM |  | HOT | FEED | GHSV | CONV. | SELE | YLD. | YLD. | PSIG. |
| HRS. | SALT | SPOT | M % | 1/HR | M % | M % | M % | WT % | HD |
| 49 | 420 | 425 | 0.59 | 1500 | 45.36 | 43.68 | 19.81 | 33.5 | 4.5 |
| 120 | 410 | 447 | 1.22 | 2000 | 80.98 | 60.07 | 48.64 | 82.2 | 20 |
| 313 | 410 | 438 | 1.31 | 2250 | 81.08 | 59.79 | 48.48 | 81.9 | 20 |
| 670 | 398 | 441 | 1.14 | 2500 | 79.88 | 62.79 | 50.15 | 84.8 | 20 |
| 1054 | 398 | 450 | 1.25 | 2500 | 79.81 | 63.52 | 50.70 | 85.7 | 20 |
|  |  |  |  | TERMINATED |  |  |  |  |  |

[(1)]Composition: VP 1.16, Mo 0.026, Zn 0.01, Li 0.01, O$_x$.
[(2)]Evaluated in a 1" × 5' salt bath reactor-3.5' bed with thermowell 3/16" × 3/16" tablets with a 1/16" hole in the center.

TABLE IX[(1,2)]

|  | TEMP C. |  | BUTANE |  | BUTANE | MAN PROD. |  |  | PRESS. |
|---|---|---|---|---|---|---|---|---|---|
| ON STREAM |  | HOT | FEED | GHSV | CONV. | SELE | YLD. | YLD. | PSIG. |
| HRS. | SALT | SPOT | M % | 1/HR | M % | M % | M % | WT % | HD |
| 70 | 420 | 425 | 0.75 | 1500 | 61.29 | 57.02 | 34.95 | 59.1 | 4.5 |
| 214 | 428 | 450 | 1.23 | 2000 | 85.02 | 55.51 | 47.20 | 79.8 | 20 |
| 406 | 415 | 438 | 1.12 | 2500 | 78.39 | 59.37 | 46.54 | 78.7 | 20 |
| 1054 | 404 | 446 | 1.33 | 2500 | 80.97 | 64.31 | 52.08 | 88.0 | 20 |
|  |  |  |  | TERMINATED |  |  |  |  |  |

[(1)]VP 1.16, Mo 0.0065, Zn 0.01, Li 0.01, O$_x$.
[(2)]Evaluated in a 1" × 5' salt bath reactor. 3.5' bed with thermowell 3/16" × 3/16" tablets with a 1/16" hole in the center.

EXAMPLE 9

The catalyst procedure used was that of Example 1 in a 12 liter flask, except that 1.79 lbs. of HCl/lb. of V₂O₅ was used. The x-ray diffraction of the calcined catalyst (2.94d/5.68d) was 2.1 with a 77% crystallinity. The surface area of the tableted catalyst was 11.4 m²/g. The conditions and summarized results are set out in TABLE X.

TABLE VII[(1,2)]

|  | TEMP C. |  | BUTANE |  | BUTANE | MAN PROD. |  |  | PRESS. |
|---|---|---|---|---|---|---|---|---|---|
| ON STREAM |  | HOT | FEED | GHSV | CONV. | SELE | YLD. | YLD. | PSIG. |
| HRS. | SALT | SPOT | M % | 1/HR | M % | M % | M % | WT % | HD |
| 48 | 420 | 423 | 0.59 | 2000 | 85.42 | 57.25 | 48.90 | 82.7 | 20.0 |
| 381 | 411 | 435 | 1.36 | 2375 | 79.17 | 61.21 | 48.46 | 81.9 | 20.0 |
| 861 | 403 | 428 | 1.33 | 2500 | 79.26 | 69.91 | 55.41 | 93.6 | 20.0 |
| 1077 | 405 | 432 | 1.31 | 2500 | 79.51 | 68.27 | 54.28 | 91.7 | 20.0 |
|  |  |  |  | TERMINATED |  |  |  |  |  |

[(1)]VP 1.16, Mo 0.013, Zn 0.01, Li 0.01, O$_x$. MoO₃ added at reflux followed by stripping of the alcohol without digestion.
[(2)]Evaluated in a 1" × 5' reactor-3.5' bed with thermowell-3/16" × 3/16" tablets with a 1/16" hole in the center.

EXAMPLE 10

The catalyst procedure used was that of Example 1 in a 12 liter flask, except that 2.5 lbs. of HCl/lb of $V_2O_5$ was used. The x-ray diffraction of the calcined catalyst (2.94d/5.68d) was 1.69 with a 80% crystallinity. The surface area of the tableted catalyst was 6.4 m²/g. The conditions and summarized results are set out in TABLE XI.

EXAMPLE 11

The catalyst was prepared by the procedure of example 10, except that the HCl- $V_2O_5$ reaction was made one day and allowed to stand overnight. The next day the Mo, Zn, Li and phosphoric acid were added and the catalyst completed. X-ray diffraction data of the calcined catalyst showed a reflection ratio (2.94d/5.68d) of 3.9, and crystallinity of 63%. Surface area of the tableted catalyst was 9.1 m²/g. The conditions and summarized results are set out in TABLE XII.

EXAMPLE 12

This catalyst prepared by the procedure of Example 1, except that a lower P:V ratio was used. This catalyst appears to be as good as that of Example 1. The conditions and summarized results of the evaluation of this catalyst are set out in TABLE XIII.

A similar catalyst was made with a higher P/V ratio than the catalyst of Example 1 and was found to have good selectivity but was not as active as either of the other two as shown in TABLE XIV.

TABLE X[1,2]

| ON STREAM HRS. | TEMP C. SALT | TEMP C. HOT SPOT | BUTANE FEED M % | GHSV 1/HR | BUTANE CONV. M % | MAN PROD. SELE M % | MAN PROD. YLD. M % | MAN PROD. YLD. WT % | PRESS. PSIG. HD | PRESS. PSIG. EXIT |
|---|---|---|---|---|---|---|---|---|---|---|
| 51 | 420 | 425 | 1.10 | 1500 | 46.67 | — | — | — | 7 | 4 |
| 196 | 413 | 426 | 1.52 | 2250 | 77.01 | 61.10 | 47.60 | 80.5 | 20 | 16.3 |
| 555 | 421 | 450 | 1.56 | 2500 | 80.45 | 64.08 | 51.55 | 87.1 | 20 | 15.5 |
| 987 | 421 | 450 | 1.67 | 2500 | 79.31 | 65.59 | 52.02 | 87.0 | 20 | 15.5 |
| TERMINATED | | | | | | | | | | |

[1] Catalyst prepared in a 12 liter flask using 1.79 lbs HCl/lb of $V_2O_5$.
[2] Evaluated in a 1" × 12' salt bath reactor. 10.5' bed with thermowell 3/16" × 3/16" tablets with a 1/16" hole in the center.

TABLE XI[1,2]

| ON STREAM HRS. | TEMP C. SALT | TEMP C. HOT SPOT | BUTANE FEED M % | GHSV 1/HR | BUTANE CONV. M % | MAN PROD. SELE M % | MAN PROD. YLD. M % | MAN PROD. YLD. WT % | PRESS. PSIG. HD | PRESS. PSIG. EXIT |
|---|---|---|---|---|---|---|---|---|---|---|
| 47 | 410 | 412 | 0.57 | 1500 | 53.75 | 53.75 | 28.89 | 48.8 | 7 | 4 |
| 240 | 411 | 426 | 1.49 | 2250 | 79.96 | 65.28 | 52.20 | 88.2 | 20 | 16.3 |
| 522 | 412 | 447 | 1.58 | 2500 | 81.10 | 65.46 | 53.09 | 89.7 | 20 | 15.5 |
| 928 | 405 | 442 | 1.58 | 2500 | 81.11 | 68.14 | 55.27 | 93.4 | 20 | 15.5 |
| TERMINATED | | | | | | | | | | |

[1] Catalyst evaluated in a 1" × 12' salt bath reactor. 10.5' bed with thermowell-3/16" × 3/16" tablets with a 1/16" hole in the center.
[2] This was a 12 liter batch made using 2.5 lbs. of HCl/lb. of $V_2O_5$.

TABLE XII[1,2]

| ON STREAM HRS. | TEMP C. SALT | TEMP C. HOT SPOT | BUTANE FEED M % | GHSV 1/HR | BUTANE CONV. M % | MAN PROD. SELE M % | MAN PROD. YLD. M % | MAN PROD. YLD. WT % | PRESS. PSIG. HD | PRESS. PSIG. EXIT |
|---|---|---|---|---|---|---|---|---|---|---|
| 45 | 400 | 402 | 0.59 | 1500 | 84.52 | 53.70 | 45.39 | 76.7 | 7 | 4 |
| 172 | 408 | 426 | 1.35 | 2000 | 79.31 | 63.69 | 50.51 | 85.4 | 20 | 17 |
| 456 | 418 | 446 | 1.47 | 2500 | 83.98 | 61.16 | 51.36 | 86.8 | 20 | 15.5 |
| 886 | 394 | 422 | 1.47 | 2500 | 84.06 | 66.72 | 56.09 | 94.8 | 20 | 15.5 |
| TERMINATED | | | | | | | | | | |

[1] Catalyst evaluated in a 1" × 12' salt bath reactor. 10.5' bed with thermowell 3/16" × −3/16" tablets with 1/16" hole in the center.
[2] $V_2O_5$ reacted with HCl (2.5#/#$V_2O_5$) in a 12 liter flask and allowed to stay at room temperature overnight before adding $MoO_3$ and other components.

TABLE XIII[1,2]

| ON STREAM HRS. | TEMP C. SALT | TEMP C. HOT SPOT | BUTANE FEED M % | GHSV 1/HR | BUTANE CONV. M % | MAN PROD. SELE M % | MAN PROD. YLD. M % | MAN PROD. YLD. WT % | PRESS. PSIG. HD |
|---|---|---|---|---|---|---|---|---|---|
| 43 | 410 | 410 | 0.66 | 1500 | 82.6 | 52.1 | 43.0 | 72.7 | 4.5 |
| 200–300 | 410 | 453 | 1.16 | 2500 | 80.5 | 61.9 | 49.8 | 84.2 | 20.0 |
| 600–700 | 396 | 432 | 1.37 | 2500 | 82.1 | 64.9 | 53.3 | 90.0 | 20.0 |
| 900–1000 | 389 | 419 | 1.26 | 2500 | 82.1 | 68.4 | 56.2 | 94.9 | 20.0 |
| 1500–1600 | 381 | 416 | 1.28 | 2500 | 81.32 | 70.31 | 57.18 | 96.6 | 20.0 |
| 2660 | 380 | 420 | 1.18 | 2500 | 82.98 | 67.21 | 55.77 | 94.3 | 20.0 |
| TERMINATED | | | | | | | | | |

[1] VP 1.124, Mo 0.013, Zn 0.01, Li 0.01. $O_x$.
[2] 1" × 5' reactor-3.5' bed with thermowell-3/16" × 3/16" tablets with 1/16" hole in center.

TABLE XIV[1,2]

| ON STREAM HRS. | TEMP C. SALT | TEMP C. HOT SPOT | BUTANE FEED M % | GHSV 1/HR | BUTANE CONV. M % | MAN PROD. SELE M % | MAN PROD. YLD. M % | MAN PROD. YLD. WT % | PRESS. PSIG. HD |
|---|---|---|---|---|---|---|---|---|---|
| 48 | 430 | 430 | 0.68 | 1500 | 49.6 | 41.3 | 20.5 | 34.6 | 4.5 |
| 250–350 | 408 | 434 | 1.19 | 2500 | 77.6 | 63.0 | 48.9 | 82.6 | 20.0 |
| 650–750 | 407 | 439 | 1.29 | 2500 | 79.3 | 63.5 | 50.3 | 85.1 | 20.0 |
| 1050–1150 | 407 | 437 | 1.32 | 2500 | 81.0 | 66.0 | 53.5 | 90.4 | 20.0 |
| TERMINATED | | | | | | | | | |

[1] VP 1.18, Mo 0.013, Zn 0.01, Li 0.01, $O_x$.
[2] Evaluated in a 1" × 12' reactor as a 10.5' bed with thermowell using 3/16" × 3/16" tablets with a 1/16" hole in the center.

The invention claimed is:

1. In a process for the partial oxidation of $C_4$–$C_{10}$ hydrocarbons to the corresponding anhydrides comprising passing a gaseous stream of said n-butane over a mixed phosphorous/vanadium/zinc/lithium/molybdenum oxide catalyst at a temperature of between 364° C. and 550° C., wherein the improvement comprises using a catalyst prepared by:
    admixing a +5 valence vanadium compound with an alcohol, contacting said mixture with gaseous HCl until the valence of vanadium is reduced to less than +5 at a temperature in the range of 35° to 60° C., digesting said reduced vanadium, a zinc compound and a lithium compound in concentrated phosphoric acid of about 98 to 101% $H_3PO_4$,
    adding a molybdenum compound in the mole ratio of Mo/V of 0.005 to 0.025:1 during said digesting,
    removing a portion of said alcohol from said digested mixture to form a slurry of mixed oxides and alcohol, and
    recovering a dried mixed oxide composition and heating said dried mixed oxide composition at a temperature in the range of 200° to 350° C. for a sufficient period to provide a mixed phosphorous/vanadium/zinc/lithium/molybdenum oxide catalyst having improved catalytic properties.

2. The process according to claim 1 wherein the mole ratio of molybdenum to vanadium of said mixed phosphorous/vanadium/zinc/lithium/molybdenum oxide oxidation catalyst is from 0.01 to 0.02:1.

3. The process according to claim 1 wherein the mole ratios of P:V, Zn:V and Li:V are 0.90 to 1.3:1, 0.001 to 0.15:1 and 0.001 to 0.15:1 respectively.

4. The process according to claim 3 wherein the mole ratios of P:V and Zn:V are 0.90 to 1.22:1 and 0.01 to 0.07:1 respectively.

5. The process according to claim 1 wherein said mixed phosphorous/vanadium/zinc/lithium/molybdenum oxide oxidation catalyst is tableted and the surface area of said tableted catalyst is less than 20 m²/g.

6. The process according to claim 5 wherein the surface area of said tableted catalyst is at least 1 m²/g.

7. The process according to claim 1 wherein said mixed phosphorous/vanadium/zinc/lithium/molybdenum oxide oxidation catalyst contains less phosphorous and has substantially equal or greater activity than the same catalyst without molybdenum.

8. The process according to claim 1 wherein molybdenum replaces a portion of said phosphorous in said mixed phosphorous/vanadium/zinc/lithium/molybdenum oxide oxidation catalyst.

9. The process according to claim 1 wherein said mixed phosphorous/vanadium/zinc/lithium/molybdenum oxide oxidation catalyst has a crystallinity of 60 to 90%.

10. The process according to claim 1 wherein said alcohol is a primary of secondary alcohol.

11. The process according to claim 1 wherein said Zn, Li, and Mo compound is each independently selected from acetate, carbonate, chloride, bromide, oxide, hydroxide or phosphate.

12. The process according to claim 10 wherein said alcohol is methanol/ethanol,1-propanol, 2-propanol, 1-butanol, 2-butanol, 2-methyl-1-propanol, 3-methyl-2-butanol, 2,2-dimethyl-1-propanol, 1-hexanol, 4-methyl-1-pentanol, 1-heptanol, 4-methyl-1-hexanol, 4-methyl-1-heptanol, 1,2-ethanediol, glycerol, trimethylopropane, diethylene glycol or triethylene glycol.

13. The process according to claim 12 wherein the alcohol comprises 2-methyl-1-propanol.

14. The process according to claim 1 wherein said Zn compound is zinc chloride, said lithium compound is lithium chloride and said molybdenum compound is molybdenum oxide.

15. A process for the partial oxidation of n-butane to maleic anhydride comprising:
    admixing a +5 valence vanadium compound with an alcohol, contacting said mixture with gaseous HCl until the valence of vanadium is reduced to less than +5 at a temperature in the range of 35° to 60° C., digesting said reduced vanadium, a zinc compound and a lithium compound in concentrated phosphoric acid of about 98 to 101% $H_3PO_4$,
    adding a molybdenum compound in the mole ratio of Mo/V of 0.005 to 0.025:1 during said digesting,
    removing a portion of said alcohol from said digested mixture to form a slurry of mixed oxides and alcohol, and
    recovering a dried mixed oxide composition and heating said dried mixed oxide composition at a temperature in the range of 200° to 350° C. for a sufficient period to provide a mixed phosphorous/vanadium/zinc/lithium/molybdenum oxide catalyst having improved catalytic properties, and
    contacting a gaseous stream of said n-butane with said mixed phosphorous/vanadium/zinc/lithium /molybdenum oxide oxidation catalyst under conditions and for a sufficient time to produce maleic anhydride.

16. The process according to claim 15 wherein said temperature is between 380° C. and 515° C.

17. The process according to claim 16 wherein said temperature is between 390° C. and 415° C.

18. The process according to claim 15 wherein said gaseous stream contains air and about 0.5 to about 2.5 mole percent n-butane.

19. The process according to claim 15 wherein the residence time calculated at standard conditions of 760 mm of mercury and 25° C. is less than about 4 seconds.

20. The process according to claim 19 wherein said residence time calculated at standard conditions of 760 mm of mercury and 25° C. is less than one second.

21. In a process for the partial oxidation of n-butane comprising passing a gaseous stream of said n-butane over a mixed phosphorous/vanadium/zinc/lithium/molybdenum oxide catalyst at a temperature of between 364° C. and 550° C., wherein the improvement comprises:

using a tableted phosphorus/vanadium/zinc/lithium mixed oxide oxidation catalyst having a surface area of at least 1 m²/g and less than 20 m²/g, a crystallinity of 60 to 90% and the mole ratio of P:V is 1.0 to 1.22:1, Zn:V is 0.01 to 0.07:1 and Li:V is 0.001 to 0.15:1 containing from 0.01 to 0.020 moles of molybdenum per mole of vanadium, characterized in that the ratio of P:V is reduced when said molybdenum is included in said ratio of 0.01 to 0.02 moles of molybdenum per mole of vanadium, thereby stabilizing the catalyst and reducing deactivation of the catalyst in reactor operation compared to an equivalent catalyst without Mo.

22. In a process for the partial oxidation of n-butane to maleic anhydride comprising passing a gaseous stream of said n-butane over a mixed phosphorous/vanadium/zinc/lithium/molybdenum oxide catalyst at a temperature of between 364° C. and 550° C., wherein the improvement comprises using a catalyst prepared by:

admixing a +5 valence vanadium compound with an alcohol, contacting said mixture with gaseous HCl until the valence of vanadium is reduced to less than +5 at a temperature in the range of 35° to 60° C., digesting said reduced vanadium, a zinc compound and a lithium compound in concentrated phosphoric acid of about 98 to 101% $H_3PO_4$, adding a molybdenum compound in the mole ratio of Mo/V of 0.005 to 0.025:1 during said digesting, removing a portion of said alcohol from said digested mixture to form a slurry of mixed oxides and alcohol, and recovering a dried mixed oxide composition and heating said dried mixed oxide composition at a temperature in the range of 200° to 350° C. for a sufficient period to provide a mixed phosphorous/vanadium/zinc/lithium/molybdenum oxide catalyst having improved catalytic properties.

* * * * *